(12) United States Patent
Antwiler

(10) Patent No.: US 8,163,555 B2
(45) Date of Patent: Apr. 24, 2012

(54) DISPOSABLE TUBING SET FOR USE WITH A CELL EXPANSION APPARATUS AND METHOD FOR STERILE SAMPLING

(75) Inventor: Glen Delbert Antwiler, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 311 days.

(21) Appl. No.: 12/706,380

(22) Filed: Feb. 16, 2010

(65) Prior Publication Data

US 2010/0144037 A1   Jun. 10, 2010

Related U.S. Application Data

(62) Division of application No. 12/021,013, filed on Jan. 28, 2008, now Pat. No. 7,718,430.

(60) Provisional application No. 60/971,382, filed on Sep. 11, 2007, provisional application No. 60/892,460, filed on Mar. 1, 2007.

(51) Int. Cl.
*C12N 5/02* (2006.01)

(52) U.S. Cl. ............ 435/383; 435/401; 435/293.1; 435/295.3

(58) Field of Classification Search .................. None
See application file for complete search history.

(56) References Cited

U.S. PATENT DOCUMENTS 4,889,812 A * 12/1989 Guinn et al. ............ 435/286.7

2002/0146816 A1   10/2002 Vellinger et al.
2008/0213894 A1   9/2008 Antwiler

FOREIGN PATENT DOCUMENTS

| WO | WO02/28996 | 4/2002 |
|---|---|---|
| WO | WO02/087491 | 11/2002 |
| WO | WO03/092573 | 11/2003 |
| WO | WO2006/026835 | 3/2006 |

OTHER PUBLICATIONS

Terumo, "Home\Products\Sterile Tubing Welders\TSCD", from Terumotransfusion.com, Apr. 7, 2008, 1 page.
International Search Report for PCT/US2008/052185, dated Jul. 3, 2008.

* cited by examiner

*Primary Examiner* — Jim Ketter
(74) *Attorney, Agent, or Firm* — John R. Merkling; Edna M. O'Connor; Elizabeth J. Reagan

(57) ABSTRACT

A disposable apparatus for cell expansion, having at least one bioreactor. The bioreactor has a cellular growth area and a supply area, the cellular growth area being separated from said supply area by a membrane. A fluid recirculation path in fluid communication with the cellular growth area allows for hermetically removing a sample containing cellular matter. This may comprise an elongated tube, or a plurality of parallel tube segments. The parallel tube segments have inflow ends and outflow ends, and the inflow ends are joined at a first common juncture and the outflow ends are joined at a second common juncture. The common junctures may comprise valves.

3 Claims, 4 Drawing Sheets

DISPOSABLE TUBING SET FOR USE WITH A CELL EXPANSION APPARATUS AND METHOD FOR STERILE SAMPLING

The present application is a divisional of U.S. patent application Ser. No. 12/021,013, filed on Jan. 28, 2008, which claims benefit under 35 U.S.C. §119(e) to U.S. Provisional Application Nos. 60/971,382, filed on Sep. 11, 2007, and 60/892,460, filed on Mar. 1, 2007, each of which is incorporated herein by reference in its entirety.

The present invention is directed toward a disposable set adapted for use with a machine for cell expansion. The disposable set consists of at least a bioreactor or cell expansion module, an oxygenator and associated bags and tubing. A cassette to aid in organizing the tubes on the machine may also be included, as well as various drip chambers, sample ports and in line filters. The invention provides a method and apparatus for taking multiple sterile samples from a cell-containing part of the set. The apparatus may include a tube having multiple parallel tube segments, from which a selected segment can be removed without interrupting the flow of fluid within the disposable set.

BACKGROUND OF THE INVENTION

Stem cells can be expanded from a few donor cells in a cell expansion apparatus. The resulting multiplied cells can be used to repair or replace damaged or defective tissues. Stem cells have broad clinical applications for a wide range of diseases. Recent advances in the area of regenerative medicine have demonstrated that stem cells have unique properties such as high proliferation rates and self-renewal capacity, ability to maintain an unspecialized cellular state, and the ability to differentiate into specialized cells under particular conditions.

As an important component of regenerative medicine, bioreactor systems play an important role in providing optimized environments for cell expansion. The bioreactor provides efficient nutrient supply to the cells and removal of metabolites, as well as furnishing a pysiochemical environment conducive to cell growth. In particular, foreign cells, such as air-borne pathogens, must be excluded from the cell-growth areas of the bioreactor. At the same time it is important to be able to obtain samples of the expanding stem cells to determine how much cellular growth has taken place. There remains a need for improved apparatus and methods for hermetically sampling expanding cellular material from cell-growth areas of a bioreactor, without environmental contamination.

SUMMARY OF THE INVENTION

The present invention comprises a disposable apparatus for cell expansion, having at least one bioreactor. The bioreactor has a cellular growth area and a supply area, the cellular growth area being separated from said supply area by a membrane. The membrane inhibits migration of cells from the cellular growth area to the supply area and permits migration of certain chemical compounds from the cellular growth area to the supply area and of certain other chemical compounds from the supply area to the cellular growth area. At least one oxygenator is in fluid communication with the supply area, and a plurality of bags is in fluid communication with the cellular growth area, the bags providing fluids to the cellular growth area. A fluid recirculation path is in fluid communication with the cellular growth area, the fluid recirculation path having means for hermetically removing a sample containing cellular matter.

The means for hermetically removing a sample may comprise an elongated tube, the length of the tube being long enough to permit at least one length containing a sample to be removed from the elongated tube. In another aspect of the invention, the means for hermetically removing a sample may comprise a plurality of parallel tube segments.

In yet another aspect, the parallel tube segments have inflow ends and outflow ends, and the inflow ends are joined at a first common juncture and the outflow ends are joined at a second common juncture. In yet another feature of the invention, the common junctures may comprise valves.

Another aspect of the invention comprises a method of expanding cellular matter, the method comprising providing at least one bioreactor, the bioreactor having a cellular growth area and a supply area, and the cellular growth area being separated from the supply area by a membrane, the membrane being adapted to inhibit migration of cells from said cellular growth area to said supply area and to permit migration of certain chemical compounds from said cellular growth area to said supply area and of certain other chemical compounds from said supply area to said cellular growth area. The method further comprises conducting a fluid containing cellular matter into the cellular growth area; providing oxygenated fluid to said supply area to maintain conditions conducive for cell growth in said cellular growth area; hermetically removing a sample containing cellular matter from a fluid recirculation path in fluid communication with said cellular growth area.

A further feature of the invention comprises providing an elongated tube, the length of the tube being long enough to permit at least one length containing the sample to be removed from the elongated tube; placing a loop of said elongated tube in a sealing device such that the tube forms an intersection with itself in said sealing device; severing the tube at said intersection to form two free ends of said tube and a looped tube segment having two ends; cauterizing the two ends of said tube segment; and sealing said two free ends of said tube together to re-connect said tube.

These and other features and advantages of the present invention will be apparent from following detailed description, taken with reference to the attached drawings and claims.

DETAILED DESCRIPTION OF THE INVENTION

Figure 1:
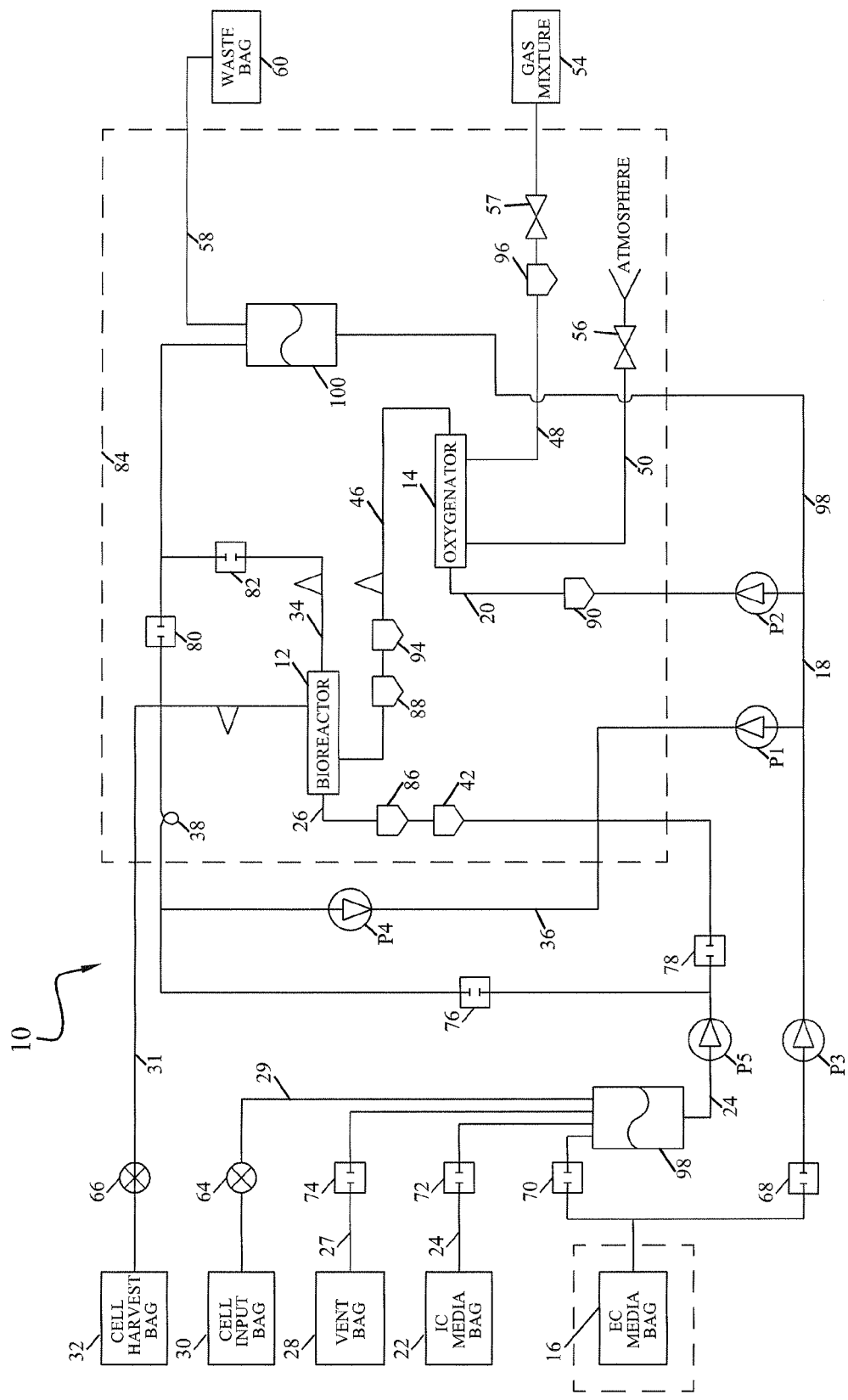
FIG. 1 is a schematic description of a cell expansion apparatus.

In the following description of the invention and in the accompanying drawings, like numerals refer to like parts.

Cell Expansion Module

A cell expansion module 12, or bioreactor, may be made of hollow fibers or flat sheet membranes enclosed in a housing. If hollow fibers are used, the fibers may be made of a biocompatible polymeric material such as Polyamix, which is a blend of polyamide, polyarylethersulfone and polyvinylpyrrolidone. Depending upon the type of cells to be expanded in the bioreactor, the fibers may or may not be treated with a substance to enhance cell growth and/or adherence to the membrane. The fibers may be held in place within the housing with polyethylene potting. The bioreactor housing has at least four openings into the interior of the housing. Two open into the intra-capillary or IC space, fluidly connecting to the interior of the hollow fibers, and two open into the extracapillary or EC space, fluidly connecting to the space surrounding the hollow fibers.

Cells may be grown in the IC space. The IC space with its minimum volume reduces the quantity of expensive media and expensive cytokines/growth factors required. The semipermeable membrane allows transfer of metabolic components, waste and gases between the EC and IC compartments. The molecular transfer characteristics of the hollow fibers are chosen to minimize loss of expensive reagents from the IC side, while allowing metabolic waste products to diffuse through the membrane into the EC side to be removed. The EC space carries nutrients to the cells in the IC space, removes waste byproducts and maintains gas balance. The bioreactor may be attached to the rest of the disposable set with connectors made of polyurethane (Tygothane C-210-A).

Oxygenator

The oxygenator 14 used may be any commercially available oxygenator. One alternative oxygenator that may be used is a hollow fiber Oxy-Cell Mate oxygenator having a fiber count of 1820, an internal fiber diameter of 280 μm, outer fiber diameter of 386 μm and an intercapillary fluid volume of 16 mL. The hollow fibers of the oxygenator are enclosed in a housing having four port openings. Inlet 20 and outlet 46 ports are fluidly connected to the interior (intercapillary or IC space) of the hollow fibers. Another set of inlet 48 and outlet 50 ports are fluidly connected to the space surrounding the hollow fibers (extracapillary or EC space).

Through the IC inlet port 20 of the oxygenator, the EC inlet line 18 is connected to deliver either fresh media from the EC media bag 16 or recirculated EC media to the oxygenator 14. Connected to the IC outlet port 46, the EC line 18 delivers oxygenated EC media to the EC inlet port 42 on the bioreactor 12. Connected to the EC inlet port 48 is a line 52 to a source of gas 54 (gas line). The EC outlet port 50 is open to the atmosphere, with a 0.22μ in-line filter 56 to prevent microbes from entering and contaminating the closed system.

EC Media Bag and EC Media Inlet Line

An EC media bag 16, which contains the media, which will flow through the EC side of the bioreactor, may be connected via a portion of flexible tubing (the EC inlet line) 18 to the IC inlet port 20 of the oxygenator 14. The EC inlet line 18 brings fresh EC media to the oxygenator 14 to be oxygenated. The EC inlet line 18 may be made of polyvinyl chloride with fluorinated ethylene propylene (PVC/FEP (sold as Tygon SE-200)).

IC Media Bag and IC Media Inlet Line

An IC media bag 22 that contains the media that will flow through the IC side of the bioreactor may be connected via a portion of flexible tubing (the IC inlet line) 24 to the IC inlet port 26 of the bioreactor 12. The IC inlet line 24 brings fresh IC media to the IC side of the bioreactor. The IC inlet line 24 may also be made of PVC/FEP.

Vent Bag

A vent bag 28 may be connected to the disposable set via flexible tubing 27 to collect any air initially in the system, before the system is filled with media and cells.

Cell Input Bag

A cell input bag 30 contains the cells to be added to the bioreactor 12. The cell input bag 30 is connected to the IC inlet line 24, which delivers cells into the lumen of the hollow fibers via cell input line 29.

Cell Harvest Bag

When the cells are ready to be harvested, they are flushed out of the IC outlet port 34 of bioreactor 12 through cell harvest line 31 and into a cell harvest bag 32.

IC Recirculation/Reseeding Tubing Loop

The disposable tubing set also may include a length of tubing which acts as an IC circulation loop 36. The IC media flows out of the bioreactor 12 from the IC outlet port 34 through tubing loop 36 and back into the bioreactor through the IC inlet port 26. This loop 36 is used to recirculate the IC media though the hollow fibers. It may also be used to flush the cells out of the hollow fibers and reseed/redistribute them throughout the hollow fibers for further growth.

The IC recirculation loop 36 may contain a sample tube 38, for example, an additional length of tubing. This additional tubing enables small pieces of the tubing to be sterilely removed from the disposable set and the media inside tested for markers of cellular metabolism such as pH, glucose, lactate, electrolytes, oxygen and carbon dioxide content. The sample tubing 38 may be made of Sanipure tubing (SEBS). The sample tube 38 may be solvent bonded into the IC loop 36 using cyclohexanone.

EC Recirculation Loop

An EC recirculation loop 40 allows the media on the EC side of the bioreactor to be recirculated. The EC recirculation loop 40 allows EC media to flow out of the bioreactor from the EC outlet port 42 back into the bioreactor through the EC inlet port 44. This loop may be used to recirculate the EC media that surrounds the hollow fibers.

Waste Bag

IC and EC media containing metabolic breakdown products from cell growth are removed from the system via tubing 58 into a waste bag 60.

Pump Loops

As shown in FIG. 1, the tubing set may engage three or more pump loops that correspond to the location of peristaltic pumps on the cell expansion apparatus. In an embodiment, the tubing set may have five pump loops, corresponding to pumps P1-P5 on the apparatus. The pump loops may be made of polyurethane (PU (available as Tygothane C-210A)).

Cassette

A cassette for organizing the tubing lines and which may also contain tubing loops for the peristaltic pumps may also be included as part of the disposable. Additional tubing lines (see 62) can be added as needed to enable specific applications such as reseeding/redistributing cells in the bioreactor. In order to control the passage of fluid through the disposable 10, manually operated clamps 64, 66 may be provided. In addition, microprocessor-controlled pinch valves 68, 70, 72, 74, 76, 80, 82 may be coupled to selected tubes of the disposable. Microprocessor-controlled pinch valves are available on blood processing devices such as the Trima® apheresis machine, available commercially from the assignee of this invention. A Trima apheresis machine may be modified to accept the disposable 10 by removing a centrifuge ordinarily mounted within the Trima apheresis machine and placing the bioreactor and oxygenator within the machine as an incubator 81. Temperature sensors 86, 88, 90 and pressure sensors 92, 94, and 96 can be connected to selected tubes of the disposable 10 and placed in electrical communication with a microprocessor (not shown). It is to be understood that pumps, temperature sensors, pressure sensors and pinch valves are preferably connected to the disposable set only temporarily by contact. Manual clamps, on the other hand, are usually mounted on their respective tubes and may be delivered with the disposable.

With the disposable apparatus 10 mounted in the incubator 81, extracorporeal media is flowed throughout the apparatus 10, including all connecting tubes, first and second drip chambers 98, 100, the oxygenator 14 and the bioreactor 12. Pumps P1, P2, P3 and P4, controlled by the incubator 18 may be selectively activated to force fluid into sections of the disposable apparatus to prime the apparatus. After priming, intercellular media and cells, for example mesenchymal stem cells may be added from bags 22, 30 through the first drip chamber 98 and conducted into a cell expansion area of the bioreactor 14 and related tubing including recirculation path 36 and sample means 38. The hermetically sealed condition of the apparatus 10 is maintained by providing a vent bag 28 coupled to the first drip chamber 98 to accommodate variations in flow from the EC media bag 16, the IC media bag 22 and the cell input bag 30. Driven by pump P2, extra corporeal fluid passes through the oxygenator 14 where the fluid is infused with gas into a supply area of the bioreactor 12. The supply area is separated from the cell expansion area by a membrane that allows oxygen and other desirable chemical components to pass into the cell expansion area and allows waste products of the cell expansion process to pass by osmosis out of the cell expansion area while preventing cellular matter from crossing the membrane. The status of the fluid flowing through the supply area of the bioreactor is monitored by temperature sensor 88 and pressure sensor 94 as well as temperature sensor 90, which monitors the temperature of the fluid entering the oxygenator 14. An appropriate gas, such as oxygen, or a gas mixture is conducted through the oxygenator 14 at a pressure monitored by sensor 96. The gas is preferably medical grade and is also isolated from ambient air by 0.22 micron filters 56, 57. The characteristics of the extracorporeal fluid can also be checked by withdrawing fluid samples through sample ports S1 and S2 on the inflow and outflow lines of the bioreactor. The sample ports have internal filters that allow fluid to be extracted by cellular sized particles from passing into or out of the apparatus 10.

The pumps are preferably peristaltic pumps. In addition to the manual clamps and automatically controlled valves, the pumps also act as valves, preventing flow of fluid past the pump when the pump is not actively driven. Therefore, when pump P1 is not in operation and valves 76, 78 are closed, a recirculation loop is formed through the bioreactor 12 and pump P4. Conditions in this recirculation loop, where cells are growing, are monitored with temperature sensor 86 and pressure sensor 92 and by taking fluid samples through a sample port S3. The fluid extracted through the sample port S3, as explained above, does not contain cells or particles of cellular size. It is important to be able to monitor the progress of cellular growth over time without compromising the hermetically sealed conditions of the apparatus 10. Once the desired cell concentrations have been obtained, the contents of the bioreactor 12 can be harvested into the cell harvest bag 32.

The sample tube 38 allows discrete samples of cell-containing fluid to be removed from the cell expansion area from time to time. The samples may then be tested to determine the state of cell growth in the cell expansion area. One embodiment of a sample tube 38 is illustrated in greater detail in FIG. 2. The sample tube 38 comprises two or more branches 110, 112, 114. One or more of the branches may be provided with a releasable clamp 116 for temporarily stopping fluid flow through the selected branch. Alternatively, other closure means, such as a hemostat, could be used. Preferably, flow is directed through a selected branch 114 by stopping the flow through other branches. When a stable flow has been established such that the contents of the selected branch reasonably represent the general contents of fluid in the cell expansion area, at least one other branch may be opened and the selected branch closed. This maintains flow through the tubing. The selected branch 114 can then be removed by application of an RF sealer (not shown) at opposite ends 118, 120 of the branch. The resulting tube segment contains a fluid sample, preferably about 1 mL in volume. Both the tube segment and the remaining portions of the apparatus 10 remain hermetically sealed.

In is not necessary to remove a complete branch to obtain a sample. The branches may be made long enough such that multiple samples can be taken. In a preferred embodiment comprising two branches, a sample may be taken from a first branch that is closed by a clamp or hemostat, while fluid continues to flow through a second branch. The free ends of the first branch are re-connected, as further described below. When a second sample is to be taken, the clamp or hemostat could be placed on the second branch, the sample could be removed, and the free ends of the second branch could be re-connected, in the same manner as the first branch. Additional samples could then be taken, alternating between the first and second branches. This maintains a similar length for both branches. Moreover, since fluid flow in both branches is restored between samples, there is little likelihood of a stagnant area forming in the flow path.

Figure 3:
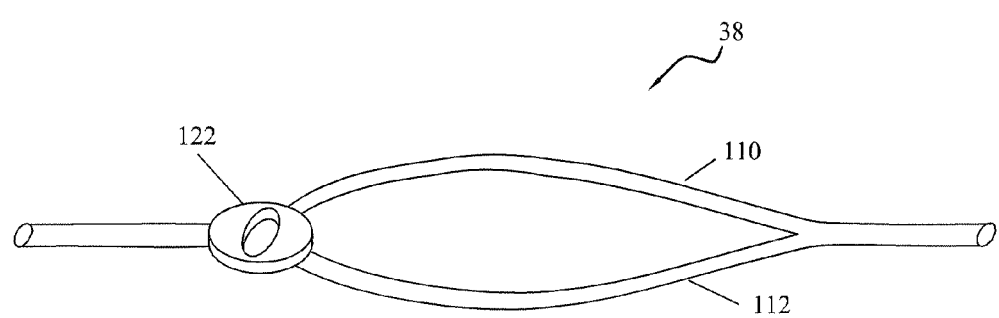
FIG. 3 is a further perspective view of the means for removing a cellular sample, with a valve.

In an alternative embodiment shown in FIG. 3, a valve 122 may be substituted for the clamp 116.

Figure 2:
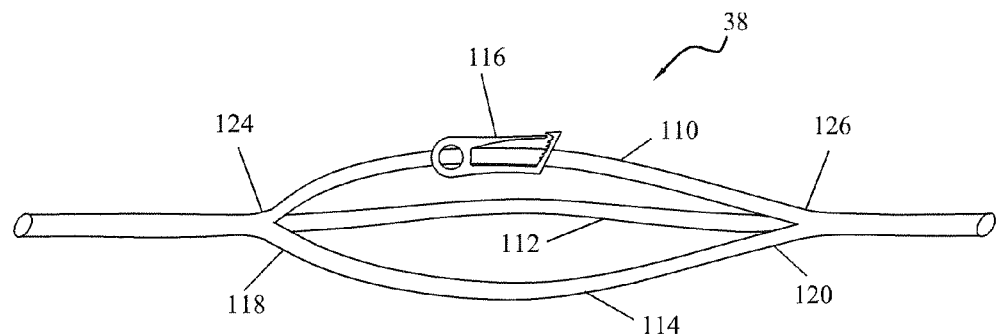
FIG. 2 is a perspective view of a means for removing a cellular sample from a cell expansion side of a cell expansion apparatus.
Figure 4:
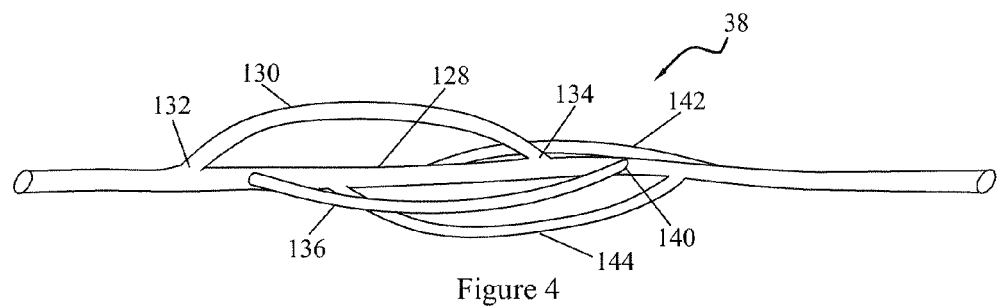
FIG. 4 is a further example of means for removing a fluid sample.

The branches 110, 112, 114 may join at common junctions 124, 126, as shown in FIG. 2, or may be spaced serially around a central tube 128, as shown in FIG. 4. A first branch 130 may exit the central tube 128 at a first outlet 132 and return to the central tube at a first inlet 134. A second branch 136 may exit the central tube at a second outlet 138, spaced linearly downstream from the first outlet 132 and radially displaced around the tube from the first outlet. The second branch 136 may return to the central tube at a second inlet 140, likewise downstream and radially displaced from the first inlet 134. This pattern may be replicated for a third branch 142, a fourth branch 144, and so on for as many branches as desired. A branch may be removed for a sample by cauterizing the branch near its outlet and inlet, as explained above.

Figure 5:
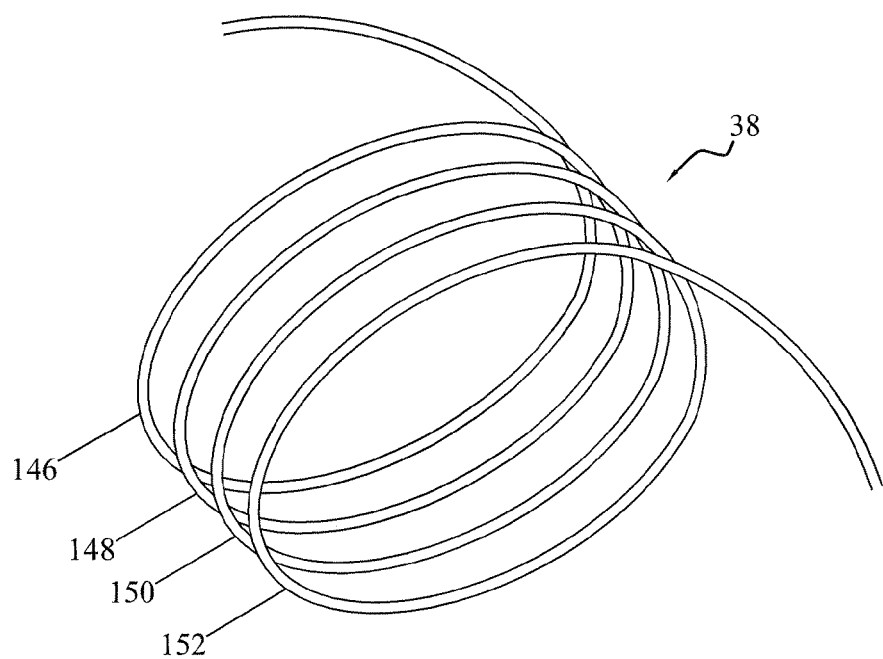
FIG. 5 is a perspective view of a coil of tubing.
Figure 6:
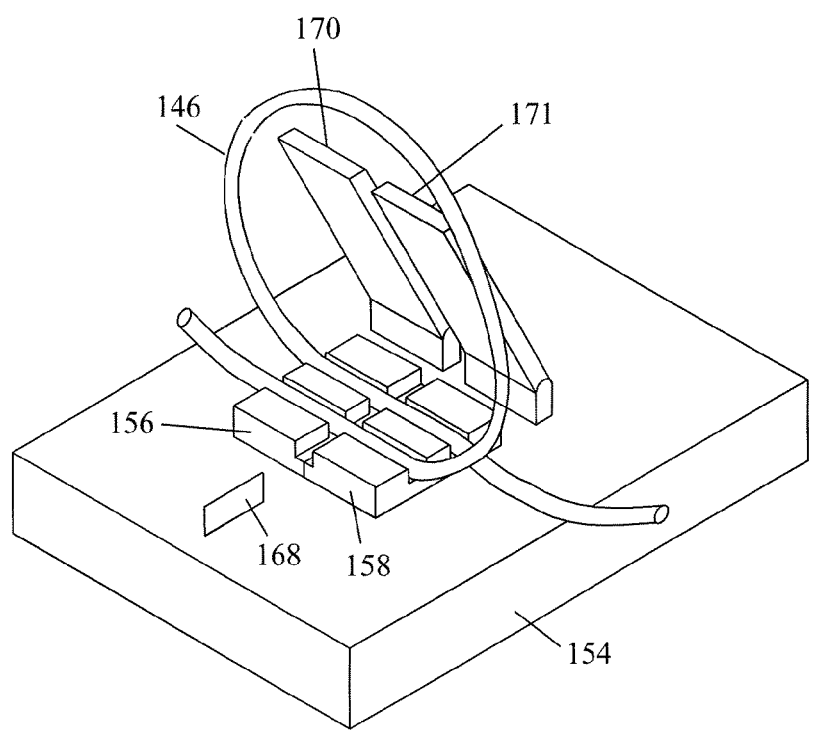
FIG. 6 is a perspective view of a tubing sealer
Figure 7:
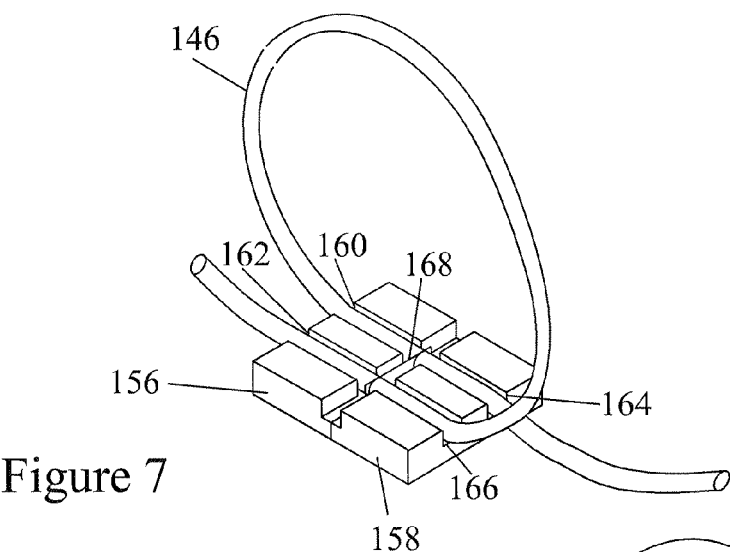
FIG. 7 is a top view of a portion of the sealer of FIG. 6.
Figure 8:
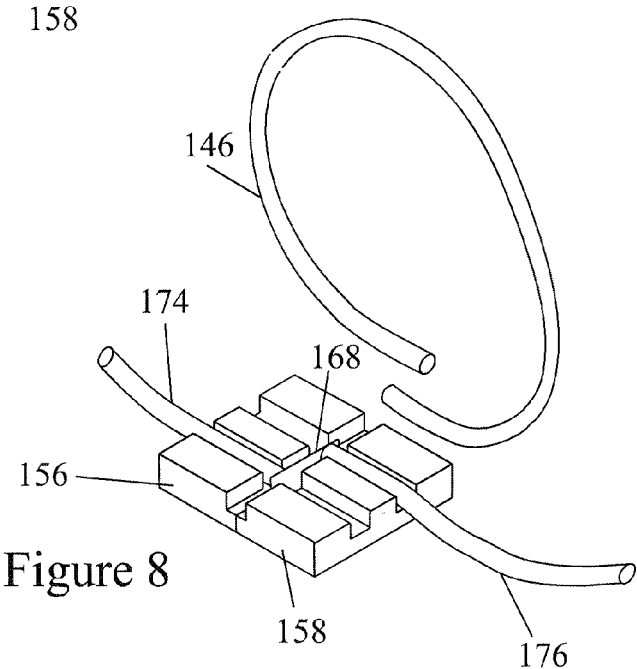
FIG. 8 is a further top view of the portion of the sealer of FIG. 7.
Figure 9:
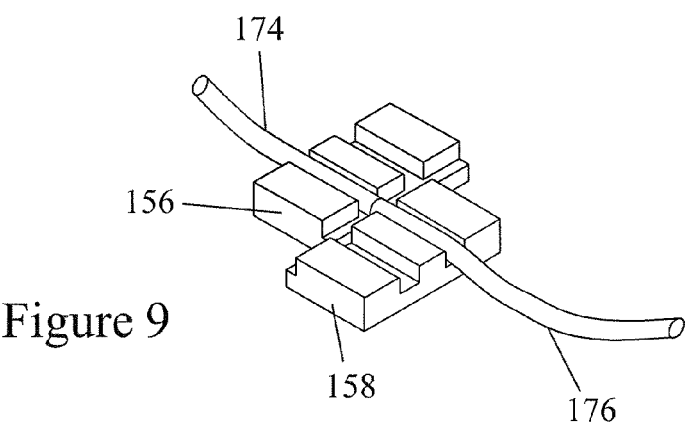
FIG. 9 is a further top view of the portion of the sealer of FIGS. 6 through 8.

A further embodiment, illustrated in FIGS. 5 through 9, comprises a method for removing a tube segment containing a cellular sample from an elongated tube. As shown in FIG. 5, the sample tube 38 may be elongated substantially more than necessary to connect apparatus in the disposable set 10. The additional length of the tube may be stored in a plurality of loops 146, 148, 150, 152. When a sample containing cellular material is needed, a loop 146 is placed in a tubing welder 154, such as tubing welders available from Terumo Medical Corporation, Somerset, N.J. The welder 154 may have slidable tube supports 156, 158, which have parallel slots for receiving tubes. Initially, slots 160 and 162 in a first tube support 156 are aligned with slots 164 and 166 in second tube support 158. Latches 170, 171 are closed over the respective tube supports 156, 158, holding the tube and its loop 146 in place. The latches 170, 171 are not shown in FIGS. 7, 8 and 9, to more clearly show the position of the tube. A disposable copper welding wafer is inserted into a gap 172 between the tube supports 156, 158 from a magazine (not shown) in the tubing welder 154. The wafer is electrically heated to cut, cauterize and seal the ends of the tube. With the heated wafer dividing the tube, the loop 146 containing the desired sample can be removed from the welder. The supports 156, 158 are then offset until a second slot 162 of the first support 156 aligns with a first slot of the second support 158, whereby cut ends 174, 176 of the tube are adjacent each other. The wafer 168 can then be removed and heated ends of the tube melt together. Fluid can then resume flow in the tube. Additional samples may be taken from time to time as long as there is sufficient length of tube to form the required loop.

The described apparatus and method can be used to collect a fluid sample containing cellular matter from a cellular expansion system. When sufficient cell replication has taken place, as determined by analysis of the sample, the contents of the bioreactor can be harvested into the cell harvest bag 32. The expanded cellular material would then be available for therapeutic and other purposes.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

I claim:

1. A method of expanding cellular matter, said method comprising providing at least one bioreactor, said bioreactor having a cellular growth area and a supply area, said cellular growth area being separated from said supply area by a membrane, said membrane being adapted to inhibit migration of cells from said cellular growth area to said supply area and to permit migration of certain chemical compounds from said cellular growth area to said supply area and of certain other chemical compounds from said supply area to said cellular growth area;
   conducting a fluid containing cellular matter into said cellular growth area;
   providing oxygenated fluid to said supply area to maintain conditions conducive for cell growth in said cellular growth area;
   providing a plurality of parallel tube segments, said parallel tube segments having inflow ends and outflow ends, and said inflow ends are joined at a first common juncture comprising a valve and said outflow ends are joined at a second common juncture;
   flowing fluid containing cellular matter through at least a first segment;
   interrupting flow through said first segment while simultaneously flowing said fluid through a second segment; and
   hermetically removing said first segment, said first segment containing a sample containing cellular matter from a fluid recirculation path in fluid communication with said cellular growth area.

2. The method of claim 1 further comprising providing an elongated tube, the length of said tube being long enough to permit at least one length containing said sample to be removed from said elongated tube;
   placing a loop of said elongated tube in a sealing device such that said tube forms an intersection with itself in said sealing device;
   severing said tube at said intersection to form two free ends of said tube and a looped tube segment having two ends;
   cauterizing the two ends of said tube segment; and
   sealing said two free ends of said tube together to reconnect said tube.

3. The method of claim 1 further comprising sampling non-cellular matter from said apparatus at least one sample port, said sample port being adapted to allow only non-cellular matter to be sampled.

* * * * *